: US009226793B2

(12) United States Patent
Jimenez

(10) Patent No.: US 9,226,793 B2
(45) Date of Patent: Jan. 5, 2016

(54) SYSTEM AND METHOD FOR SELECTIVELY ENERGIZING CATHETER ELECTRODES

(71) Applicant: BIOSENSE WEBSTER, INC., Diamond Bar, CA (US)

(72) Inventor: Eduardo Jimenez, Paramount, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 14/081,957

(22) Filed: Nov. 15, 2013

(65) Prior Publication Data

US 2014/0243816 A1 Aug. 28, 2014

Related U.S. Application Data

(63) Continuation of application No. 12/985,254, filed on Jan. 5, 2011, now Pat. No. 8,603,085, which is a continuation of application No. 11/322,591, filed on Dec. 30, 2005, now Pat. No. 7,879,029.

(51) Int. Cl.
*A61B 18/14* (2006.01)
*A61B 18/12* (2006.01)
*A61B 17/00* (2006.01)
(Continued)

(52) U.S. Cl.
CPC ......... *A61B 18/1492* (2013.01); *A61B 18/1206* (2013.01); *A61B 2017/00026* (2013.01); *A61B 2018/00029* (2013.01); *A61B 2018/00351* (2013.01); *A61B 2018/00577* (2013.01); *A61B 2018/00875* (2013.01); *A61B 2018/124* (2013.01); *A61B 2018/1467* (2013.01); *A61B 2019/5251* (2013.01)

(58) Field of Classification Search
CPC ............. A61B 2018/00577; A61B 2018/1467; A61B 2018/1492
USPC .......................................................... 606/41
See application file for complete search history.

(56) References Cited

U.S. PATENT DOCUMENTS 4,365,639 A * 12/1982 Goldreyer ...................... 607/122
4,532,924 A * 8/1985 Auth et al. ....................... 606/50
4,630,611 A * 12/1986 King .............................. 600/377
(Continued)

FOREIGN PATENT DOCUMENTS

| | | |
|---|---|---|
| CA | 2 285 342 | 10/1998 |
| EP | 0 974 936 | 1/2000 |

(Continued)

OTHER PUBLICATIONS

EP Communication dated Apr. 2, 2007 for EP Application No. 06256634.4 enclosing Partial European Search Report completed Mar. 19, 2007, 8 pages.

*Primary Examiner* — Lee S Cohen
(74) *Attorney, Agent, or Firm* — Christie, Parker & Hale, LLP

(57) ABSTRACT

The present invention is directed to a system, a method and a catheter that provide improved ablation capabilities and improved energy efficiency by selectively energizing catheter electrodes on the basis of impedance measurements. In particular, the invention is directed to the selective energization of catheter radial electrodes that together with a tip electrode form a generally continuous tissue contact surface, wherein the selection is made on the basis of impedance measurement as an indication of the amount of tissue contact of each radial electrode.

12 Claims, 12 Drawing Sheets

(51) Int. Cl.
*A61B 18/00* (2006.01)
*A61B 19/00* (2006.01)

(56) References Cited

U.S. PATENT DOCUMENTS

| | | | |
|---|---|---|---|
| 4,660,571 A | 4/1987 | Hess et al. | |
| 5,078,714 A | 1/1992 | Katims | |
| 5,341,807 A | 8/1994 | Nardella | |
| 5,391,199 A | 2/1995 | Ben-Haim | |
| 5,398,683 A * | 3/1995 | Edwards et al. | 600/374 |
| 5,443,489 A | 8/1995 | Ben-Haim | |
| 5,447,529 A | 9/1995 | Marchlinski et al. | |
| 5,469,857 A | 11/1995 | Laurent et al. | |
| 5,480,422 A | 1/1996 | Ben-Haim | |
| 5,546,951 A | 8/1996 | Ben-Haim | |
| 5,558,091 A | 9/1996 | Acker et al. | |
| 5,568,809 A | 10/1996 | Ben-Haim | |
| 5,662,108 A | 9/1997 | Budd et al. | |
| 5,673,704 A | 10/1997 | Marchlinski et al. | |
| 5,718,701 A * | 2/1998 | Shai et al. | 606/41 |
| 5,738,096 A | 4/1998 | Ben-Haim | |
| 5,755,761 A * | 5/1998 | Obino | 607/122 |
| 5,836,874 A | 11/1998 | Swanson et al. | |
| 5,836,990 A | 11/1998 | Li | |
| 5,891,095 A | 4/1999 | Eggers et al. | |
| 5,935,079 A | 8/1999 | Swanson et al. | |
| 5,964,757 A | 10/1999 | Ponzi | |
| 6,210,406 B1 | 4/2001 | Webster | |
| 6,217,574 B1 | 4/2001 | Webster | |
| 6,226,542 B1 | 5/2001 | Reisfeld | |
| 6,241,724 B1 * | 6/2001 | Fleischman et al. | 606/41 |
| 6,301,496 B1 | 10/2001 | Reisfeld | |
| 6,546,270 B1 | 4/2003 | Goldin et al. | |
| 6,569,160 B1 | 5/2003 | Goldin et al. | |
| 6,592,580 B1 * | 7/2003 | Stockert | 606/41 |
| 6,602,242 B1 | 8/2003 | Fung et al. | |
| 6,690,963 B2 | 2/2004 | Ben-Haim et al. | |
| 6,799,064 B1 * | 9/2004 | Hassett | 600/374 |

FOREIGN PATENT DOCUMENTS

| | | |
|---|---|---|
| EP | 1 502 542 A1 | 2/2005 |
| JP | 2000-201949 | 7/2000 |
| JP | 2001-510354 | 7/2001 |
| JP | 2002-65626 | 3/2002 |
| WO | WO 95/02995 | 2/1995 |
| WO | WO 96/05768 | 2/1996 |
| WO | WO 97/45157 | 12/1997 |

* cited by examiner

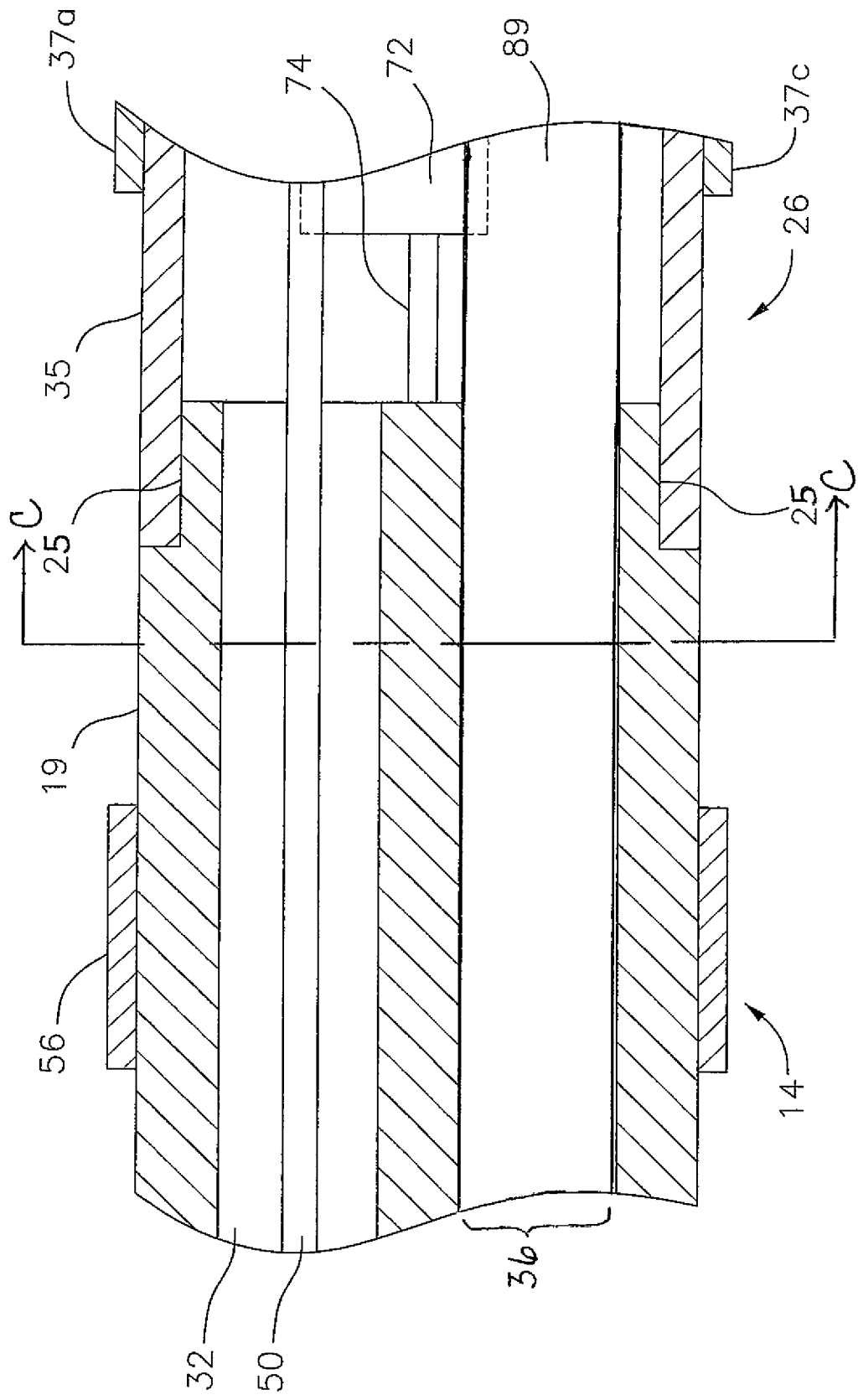

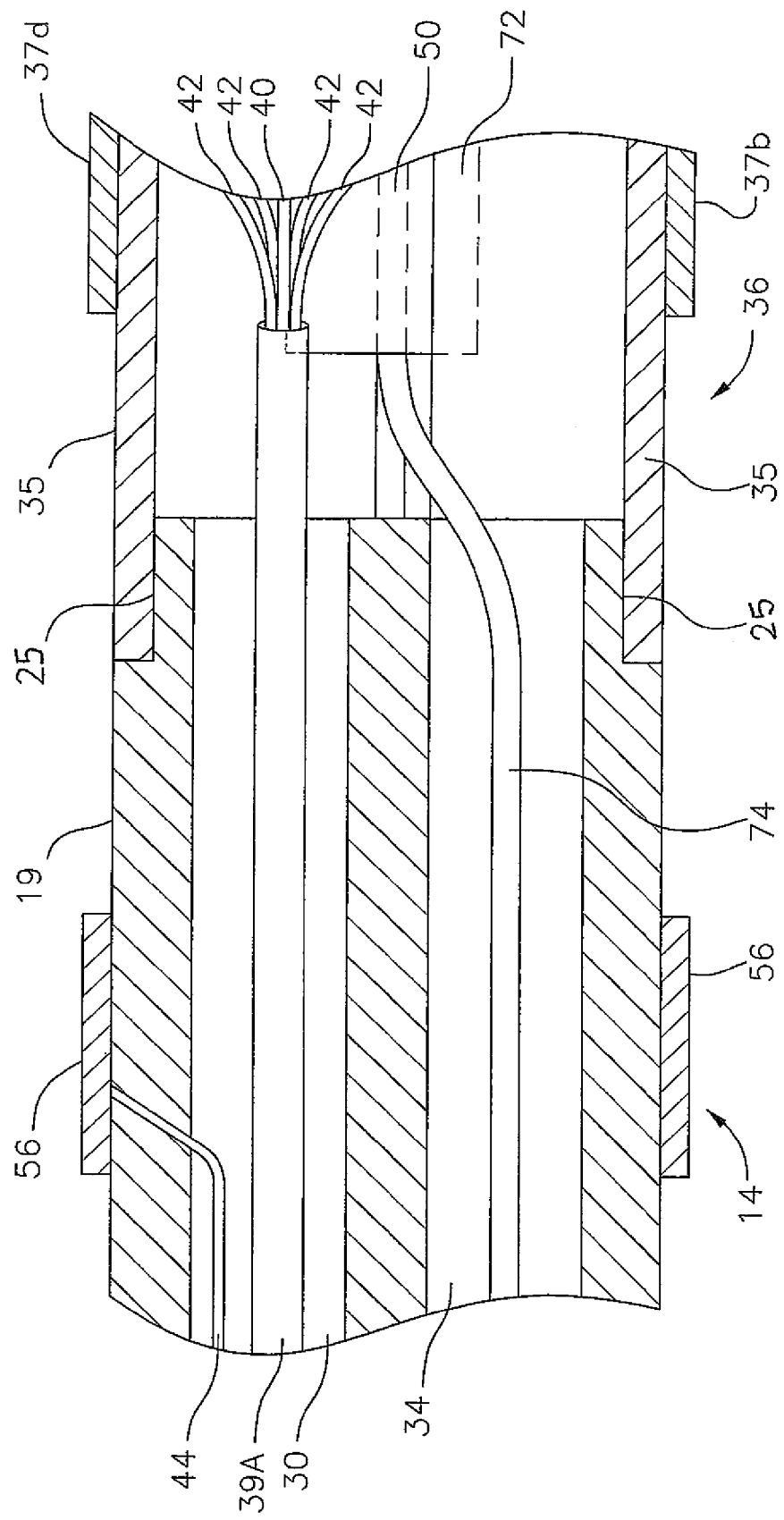

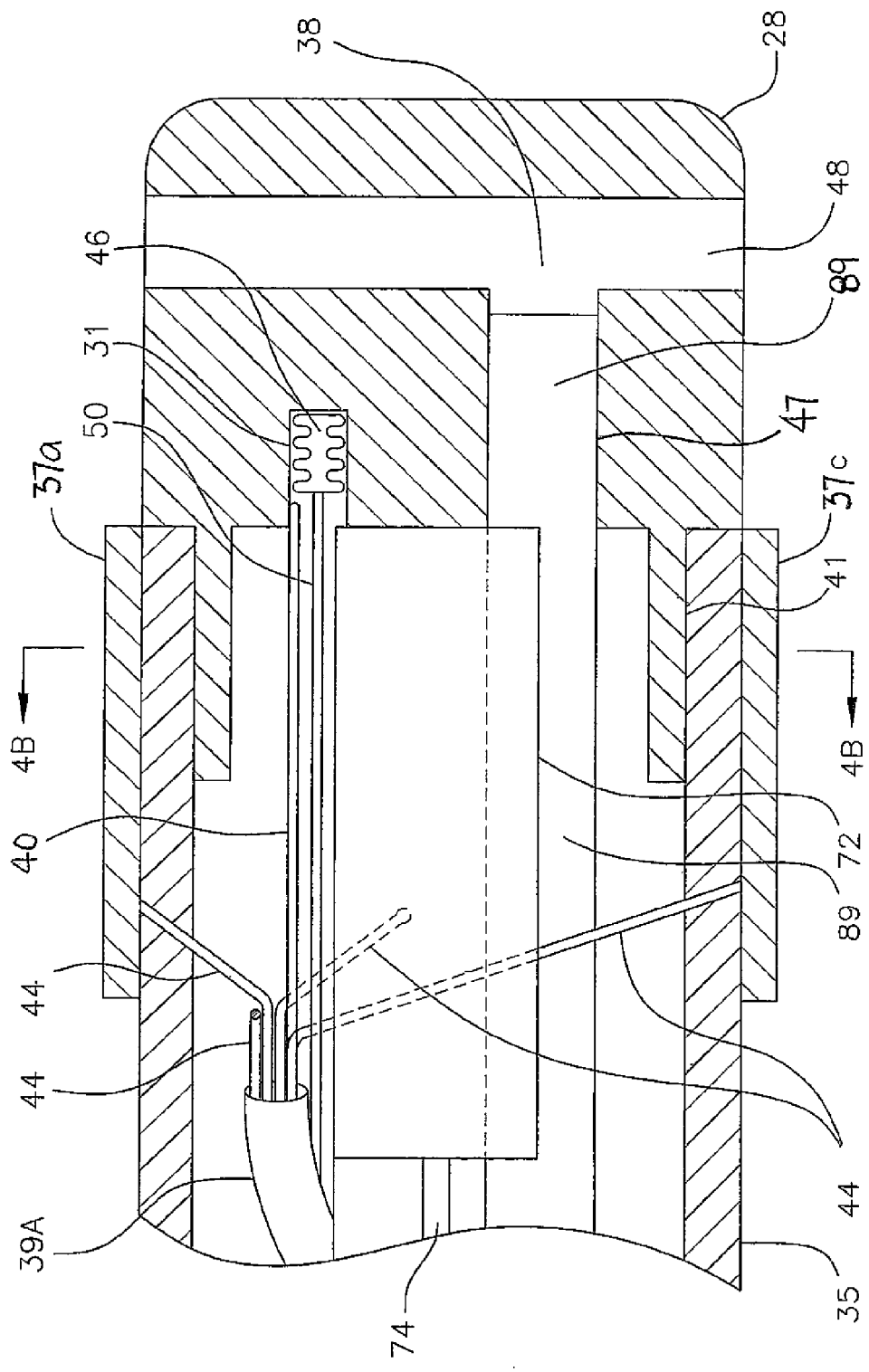

SYSTEM AND METHOD FOR SELECTIVELY ENERGIZING CATHETER ELECTRODES

CROSS-REFERENCE TO RELATED APPLICATION(S)

This application is a continuation of and claims priority to and the benefit of U.S. patent application Ser. No. 12/985,254, filed Jan. 5, 2011, now U.S. Pat. No. 8,603,085, issued Dec. 10, 2013, which is a continuation of U.S. patent application Ser. No. 11/322,591, filed Dec. 30, 2005, now U.S. Pat. No. 7,879,029, issued Feb. 1, 2011, the entire contents of which are incorporated herein by reference.

FIELD OF THE INVENTION

The present invention is directed to a catheter for electric diagnosis and treatment of the heart, and more particularly to a catheter for mapping and ablation.

BACKGROUND OF THE INVENTION

Cardiac arrhythmias, the most common of which is ventricular tachycardia (VT), are a leading cause of death. In a majority of patients, VT originates from a 1 mm to 2 mm lesion located close to the inner surface of the heart chamber. One of the treatments for VT comprises mapping the electrical pathways of the heart to locate the lesion followed by ablation of the active site.

U.S. Pat. No. 5,546,951; U.S. patent application Ser. No. 08/793,371; and PCT application WO 96/05768, which are incorporated herein in their entirety by reference, disclose methods for sensing an electrical property of heart tissue such as local activation time as a function of the precise location within the heart. The data are acquired by advancing into the heart one or more catheters that have electrical and location sensors in their distal tips. The precise three-dimensional location of the catheter tip is as ascertained by the location sensor contained therein. The location sensor operates by generating signals that are responsive to its precise location within an externally generated non-ionizing field such as an electromagnetic field. Simultaneous with the acquisition of location information, electrical information is also acquired by at least one electrode contained at the catheter distal tip. Accurate sensing of location and electrical information by sensors contained in the catheter generally requires a high degree of confidence that a catheter electrode is in contact with the tissue.

Methods of creating a map of the electrical activity of the heart based on these data are disclosed in U.S. patent application Ser. Nos. 09/122,137 and 09/357,559 filed on Jul. 24, 1998 and Jul. 22, 1999, respectively, and in European Patent Application 974,936 which are also incorporated herein in their entirety by reference. In clinical settings, it is not uncommon to accumulate data at 100 or more sites within the heart to generate a detailed, comprehensive map of heart chamber electrical activity. The use of the location sensors as hereinabove described is highly useful in providing a detailed and accurate map of the heart chamber's activity.

Catheters containing position or location sensors may also be used to determine the trajectory of points on the cardiac surface. These trajectories may be used to infer mechanical motion characteristics such as the contractility of the tissue. As disclosed in U.S. Pat. No. 5,738,096 which is incorporated herein in its entirety by reference, maps depicting such motion characteristics, which may be superimposed with maps depicting local electrical information, may be constructed when the trajectory information is sampled at a sufficient number of points in the heart. Accurate maps of such motion characteristics again require confidence that the data are acquired when the catheter tip is in contact with the cardiac tissue.

The detailed maps generated as hereinabove described may serve as the basis for deciding on a therapeutic course of action, for example, tissue ablation, to alter the propagation of the heart's electrical activity and to restore normal heart rhythm. In cardiac ablation, energy, typically in the radiofrequency (RF) range, is supplied at selected points on the intracardiac surface by a catheter having an ablation electrode at its distal tip. Ablation is effected by bringing the distal tip electrode into contact with the locus of aberrant electrical activity and by initiating the delivery of RF energy through the distal tip electrode from an external RF generator in communication with the distal tip electrode. Ablation is most effectively performed when the distal tip electrode is in contact with the cardiac wall. Absence of contact or poor contact of the tip electrode with the heart wall leads to dissipation of the RF energy in the blood, as well as possible fouling of the tip electrode with the concomitant possibility of blood clot formation. Accordingly, it is important that both mapping and ablation be accompanied by methods and systems for detecting and ensuring electrode-tissue contact.

A number of references have reported methods to determine electrode-tissue contact, including U.S. Pat. Nos. 5,935,079; 5,891,095; 5,836,990; 5,836,874; 5,673,704; 5,662,108; 5,469,857; 5,447,529; 5,341,807; 5,078,714; and Canadian Patent Application 2,285,342. A number of these references, e.g., U.S. Pat. Nos. 5,935,079, 5,836,990, 5,447,529, and 6,569,160 determine electrode-tissue contact by measuring the impedance between the tip electrode and a return electrode. As disclosed in the '160 patent, the entire disclosure of which is hereby incorporated by reference, it is generally known that impedance through blood is generally lower that impedance through tissue. Accordingly, tissue contact has been detected by comparing the impedance values across a set of electrodes to pre-measured impedance values when an electrode is known to be in contact with tissue and when it is known to be in contact only with blood.

A disadvantage of typical ablation electrodes is that it is sometimes difficult to accurately predict lesion size because the lesion size can vary depending on the orientation of the ablation electrode. For example, typically a 7 French catheter (having an outer diameter of just over 2 mm) is provided with an ablation tip electrode at its distal end having a length ranging from about 4 mm to about 8 mm. If the ablation electrode is provided in perpendicular relation to the tissue, a relatively small surface area of the electrode is in contact with the tissue. In contrast, a relatively larger surface area would be in contact with the tissue if the ablation electrode were in a generally parallel relationship to the tissue, i.e., if the ablation electrode were positioned on its side. The size of the lesion is often related to the amount surface area in contact with the tissue and there can be significant energy loss through the portion of the electrode not in contact with any tissue, particularly since blood has a higher conductivity than tissue.

Moreover, overheating of the tip electrode can cause complications, including the formation of char and/or thrombus on the electrode surface. The creation of char and thrombus is unsafe, as the char and thrombus can be dislodged from the electrode during the procedure or during removal of the catheter after the procedure.

SUMMARY OF THE INVENTION

The present invention is directed to a system, a method and a catheter that provide improved ablation capabilities and improved energy efficiency by selectively energizing catheter electrodes on the basis of impedance measurements. In particular, the invention is directed to the selective energization of catheter radial electrodes that together with a tip electrode form a generally continuous tissue contact surface, wherein the selection is made on the basis of impedance measurement as an indication of the amount of tissue contact of each radial electrode.

The system for selectively energizing electrodes on a catheter includes a catheter having a catheter body, and a tip section carrying a tip electrode and a plurality of radial electrodes and a return electrode. There are also a signal generator to provide impedance test signals and a multiplexer adapted to operate in a first mode wherein the multiplexer continuously changes electrical connection between the signal generator to a specific radial electrode, and a second mode wherein the multiplexer connects the signal electrode to a selected radial electrode. Further included in the system are an impedance measurement circuitry adapted to provide impedance measurements of each radial electrodes as an indication of tissue contact, and a microcontroller adapted to command the multiplexer to operate in said first mode or said second mode. An ablation energy source is also provided to energize the tip electrode and the selected radial electrode.

The method of the present invention includes providing a catheter having a catheter body, and a tip section carrying a tip electrode and a plurality of radial electrodes proximal the tip electrode, and providing a return electrode. The method further includes providing a signal generator adapted to generate impedance test signals, and changing electrical connection between the signal generator and a specific radial electrode. The method further includes obtaining impedance measurement for each radial electrode when it is receiving impedance test signals as an indication of tissue contact, and identifying the radial electrode with the highest impedance measurement. The method further includes maintaining electrical connection between the signal generator and the radial electrode with the highest impedance measurement the exclusion of remaining radial electrodes, and applying ablation energy to the radial electrode with the highest impedance to the exclusion of nonselected radial electrodes.

A catheter of the present invention includes a catheter body having an outer wall, proximal and distal ends, and a single central lumen extending therethrough and a control handle at the proximal end of the catheter body. Also included are a tip section comprising a segment of flexible tubing having proximal and distal ends and at least one lumen therethrough, the proximal end of the tip section being fixedly attached to the distal end of the catheter body, and a tip electrode fixedly attached to the distal end of the tubing of the tip section. Moreover, a plurality of radial electrodes are fixedly attached to the tubing immediately proximal the tip electrode, wherein each radial electrode is configured to form a specific generally continuous tissue contact surface with the tip electrode.

BRIEF DESCRIPTION OF THE DRAWINGS

These and other features and advantages of the present invention will be better understood by reference to the following detailed description when considered in conjunction with the accompanying drawings wherein:

FIG. 3A is a side cross sectional view of an embodiment of the intermediate section and a tip section taken along a first diameter;

FIG. 3B is a side cross sectional view of the intermediate section and the tip section of FIG. 3A, taken along a second diameter generally perpendicular to the first diameter;

FIG. 4A is a side cross sectional view of an embodiment of a tip section;

DETAILED DESCRIPTION OF THE INVENTION

The present invention provides a system and method and a catheter for use therewith that ablates with improved energy efficiency. The invention is directed to the selective energization of catheter radial electrodes that together with a tip electrode form a generally continuous tissue contact surface, wherein the selection is made on the basis of impedance measurement as an indication of the amount of tissue contact of each radial electrode.

Figure 1:
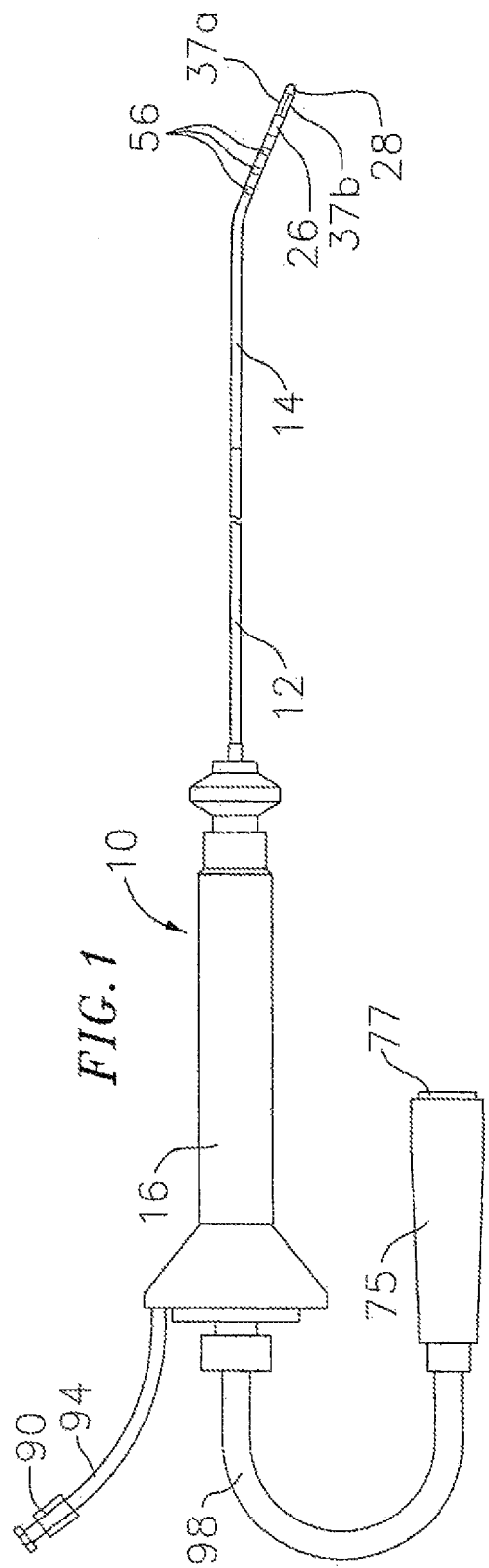
FIG. 1 is a side elevational view of an embodiment of a catheter in accordance with the present invention.

With reference to FIG. 1, the catheter 10 comprises an elongated catheter body 12 having proximal and distal ends, an intermediate section 14 at the distal end of the catheter body, a control handle 16 at the proximal end of the catheter body, and an irrigated tip section 26 at the distal end of the catheter body. The tip section carries a tip electrode 28 and a plurality of radial electrodes 37 immediately proximal the tip electrode. The tip section 26 of the catheter may also carry an electromagnetic location sensor 72 to determine the position and orientation of the catheter within the patient's body.

Figure 2:
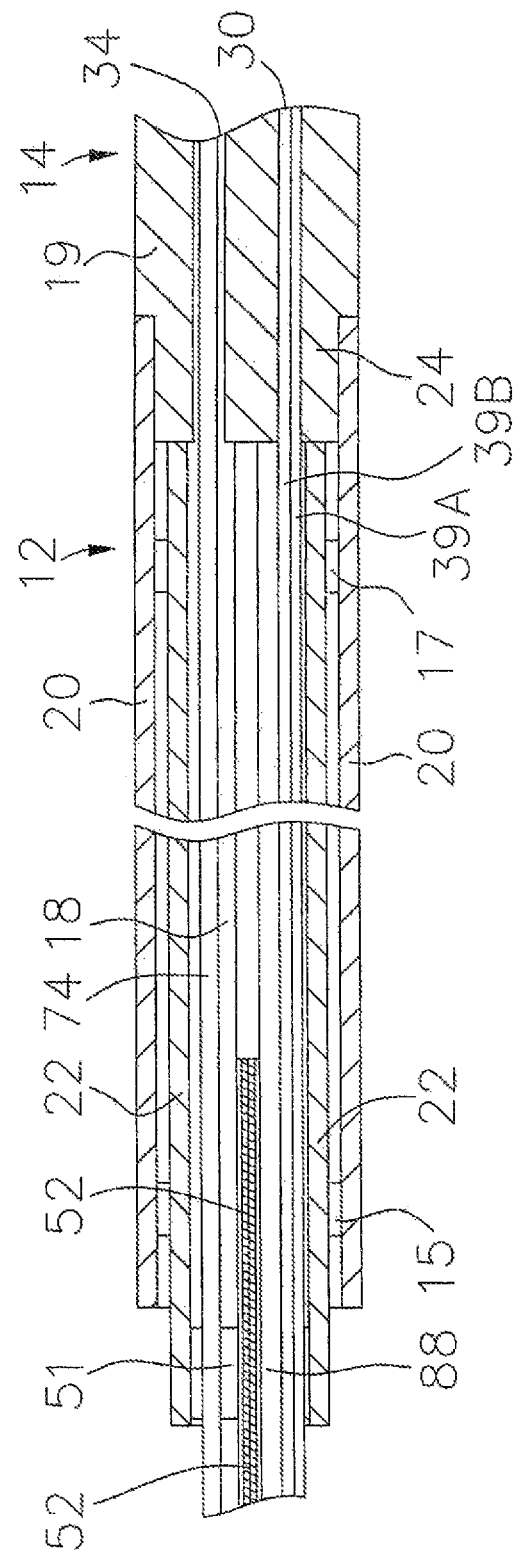
FIG. 2 is a side cross sectional view of an embodiment of a catheter body and an intermediate section taken along a first diameter.
Figure 2A:
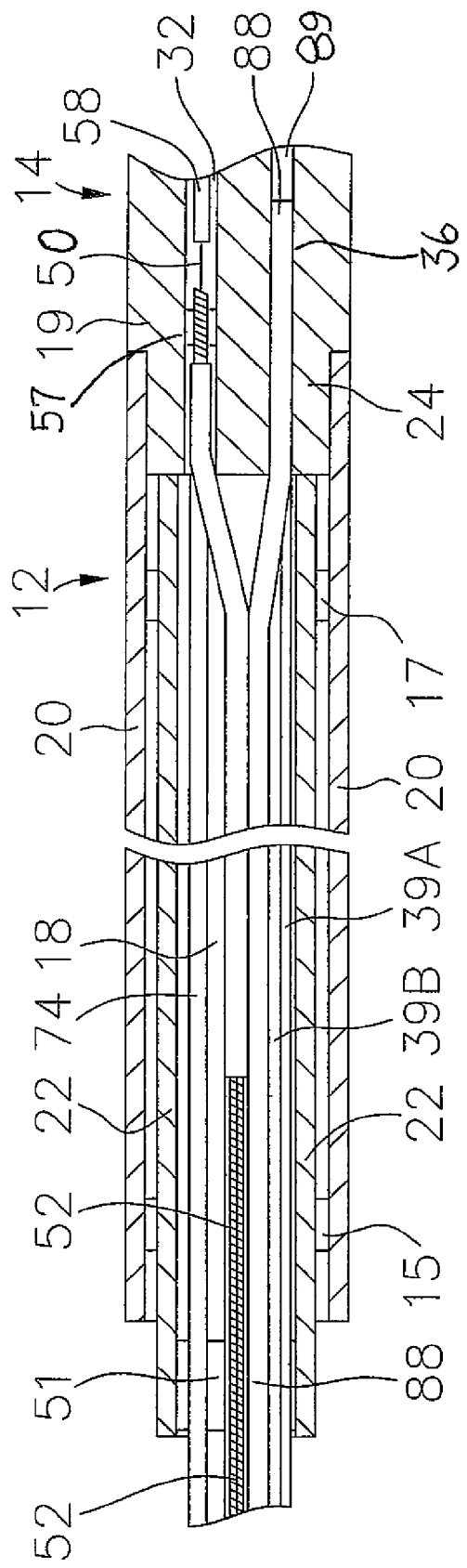
FIG. 2A is a side cross sectional view of the catheter body and intermediate section of FIG. 2 taken along a second diameter generally perpendicular to the first diameter.

With reference to FIGS. 2 and 2A, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate at least a puller wire 50, lead wires 40, 42 and 44, a first irrigating tube segment 88, a sensor cable 74. If desired, the inner surface of the outer wall 20 is lined with a stiffening tube 22 to provide improved torsional stability. The proximal end of the stiffening tube 22 is affixed to the outer wall by glue joint 15. The distal end of the stiffening tube 22 is affixed to the outer wall by glue joint 17. A particularly preferred catheter has an outer wall 20 with an outer diameter of from about 0.090 inch to about 0.94 inch and an inner diameter of from about 0.061 inch to about 0.065 inch.

Figure 3C:
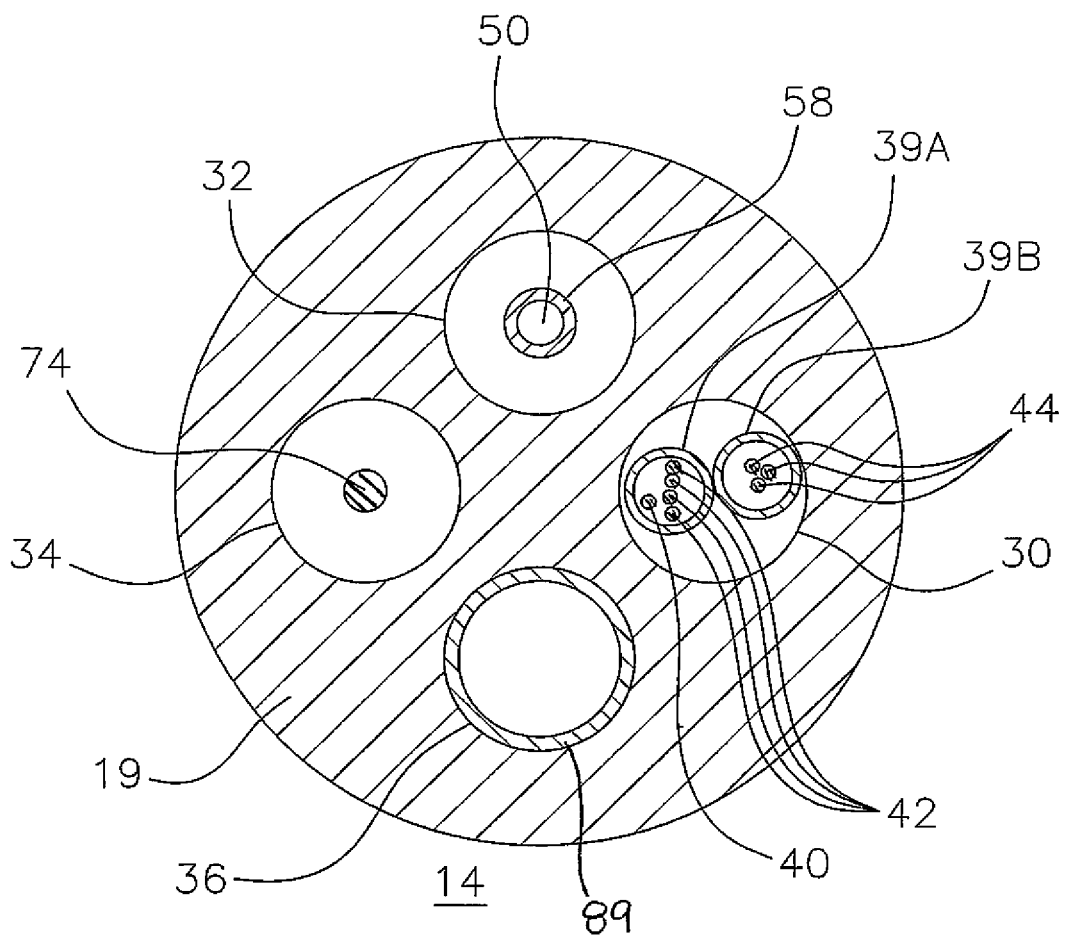
FIG. 3C is a longitudinal cross sectional view of the intermediate section of FIG. 3A, taken along line 3C-3C.

As shown in FIGS. 3A, 3B and 3C, the intermediate section 14 distal the catheter body 12 comprises a short section of tubing 19 having multiple lumens. A first lumen 30 carries the electrode lead wires 40, 42 and 44. A second lumen 32 carries the puller wire 50. A third lumen 34 carries the sensor cable 74 for the electromagnetic location sensor 72. A fourth lumen 36 allows passage of fluid transported in the first infusion tube segment 88 and carries a proximal portion of a second infusion tube 89 whose distal end is in the tip electrode 28. The tubing 19 is made of a suitable nontoxic material that is preferably more flexible than the catheter body 12. A presently preferred material for the tubing 19 is braided polyurethane, i.e., polyurethane with an embedded mesh of braided stainless steel or the like. The size of each lumen is not critical, but is sufficient to house the lead wires, puller wire, the sensor cable or any other components.

The useful length of the catheter, i.e., that portion that can be inserted into the body can vary as desired. Preferably the useful length ranges from about 110 cm to about 120 cm. The length of the intermediate section 14 is a relatively small portion of the useful length, and preferably ranges from about 3.5 cm to about 10 cm, more preferably 6 from about 5 cm to about 6.5 cm.

A preferred means for attaching the catheter body 12 to the intermediate section 14 is illustrated in FIG. 2. The proximal end of the intermediate section 14 comprises an outer circumferential notch 24 that receives the inner surface of the outer wall 20 of the catheter body 12. The intermediate section 14 and catheter body 12 are attached by glue or the like.

If desired, a spacer (not shown) can be located within the catheter body between the distal end of the stiffening tube 22 (if provided) and the proximal end of the intermediate section 14. The spacer provides a transition in flexibility at the junction of the catheter body 12 and intermediate section 14, which allows this junction to bend smoothly without folding or kinking. A catheter having such a spacer is described in U.S. Pat. No. 5,964,757, the disclosure of which is incorporated herein by reference.

Figure 4B:
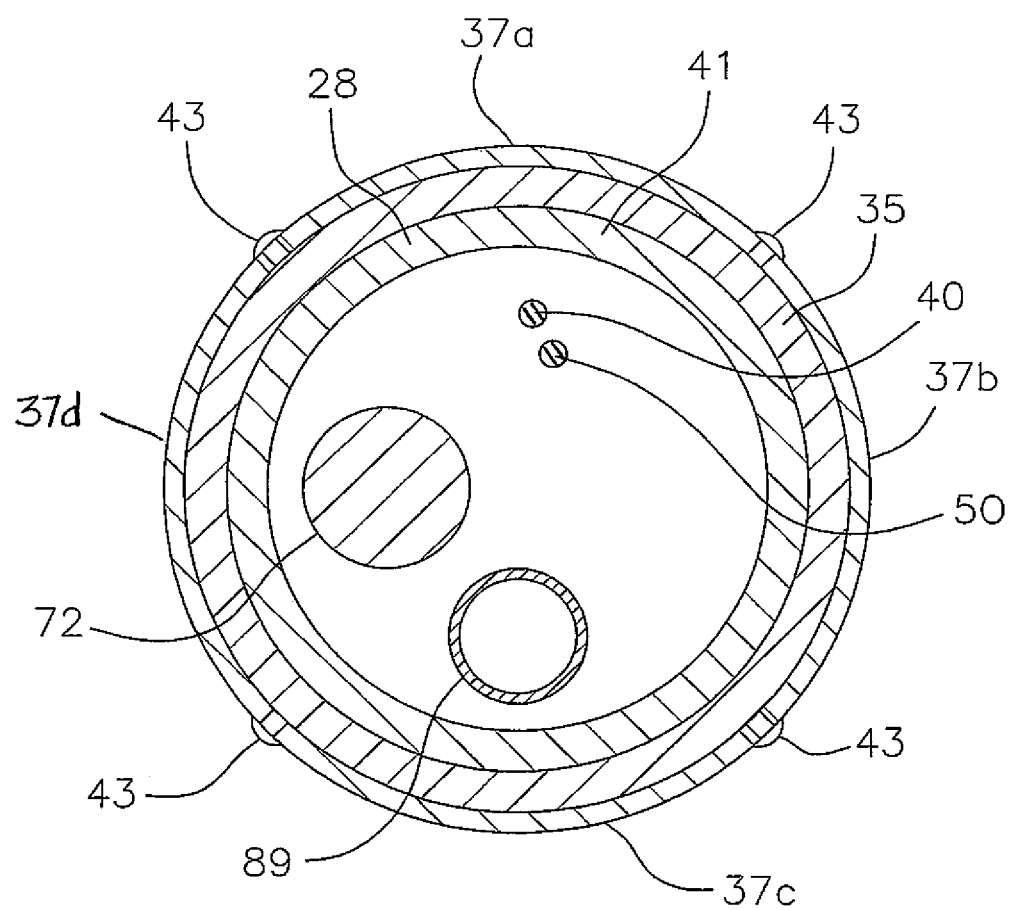
FIG. 4B is a longitudinal cross-sectional view of the tip section of FIG. 4A taken along line 4B-4B.

Referring to FIGS. 4A and 4B, at the distal end of the intermediate section 14 is the tip section 26. Preferably the tip section 26 has a diameter about the same as the outer diameter of the tubing 19. In the illustrated embodiment, the tip section 26 has the tip electrode 28 and a plastic housing or a short section of tubing 35 proximal the tip electrode 28 for housing the location sensor 72. The proximal end of the plastic housing 35 is received by a circumferential notch 25 (FIGS. 3A and 3B) formed in the distal end of the tubing 19 and is bonded thereto with polyurethane glue or the like. Preferably the plastic housing is about 1 cm long.

The tip electrode 28 is generally solid, having a fluid passage 38. In the embodiment shown, the fluid passage 38 comprises an axial branch 47 and a plurality of transverse branches 48 that extend radially from the distal end of the axial branch to the outer surface of the tip electrode 28. It is understood that the configuration of the fluid passage may vary as desired.

Formed in the proximal end of the tip electrode 28 is a blind hole 31 that generally corresponds in location to the second lumen 32 carrying the puller wire 50. As described in further detail, the distal end of the puller wire and the distal end of the lead wire 40 that connects to the tip electrode 28 can both be anchored in the blind hole 31. A preferred tip electrode has an effective length, i.e., from its distal end to the distal end of the tubing 35, of about 3.5 mm, and an actual length, i.e., from its distal end to its proximal end, of about 4.0 mm.

The tip electrode 28 is attached to the plastic housing 35 by a stem 41 formed in the proximal end of the tip electrode 28, which is received by the distal end of the tubing 35. The stem 41 is affixed with adhesive, glue or the like. The puller wire 50 and the lead wire 40 help keep the tip electrode 28 in place on the tip section 26.

Figure 5:
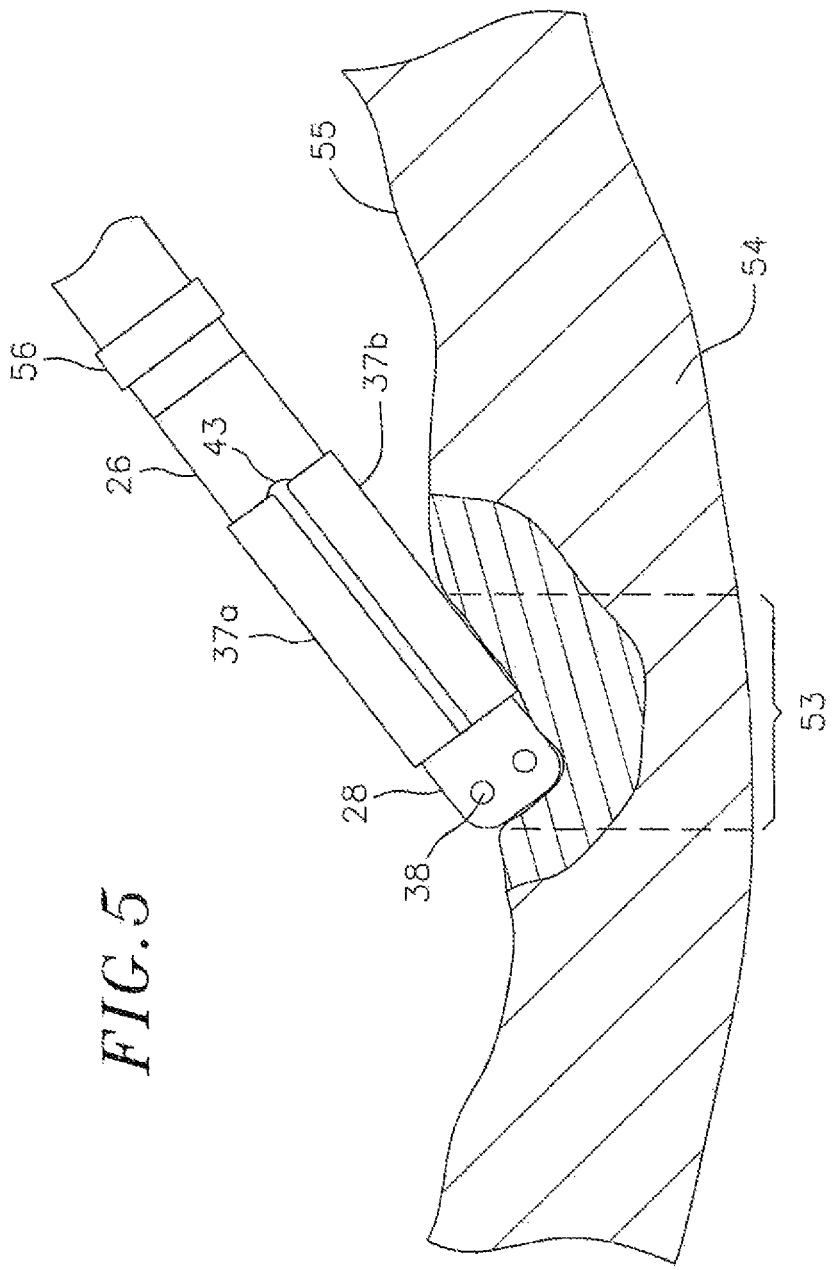
FIG. 5 is a schematic perspective view of an embodiment of the catheter of the present invention in tissue contact for ablating and creating a lesion.

In accordance with the present invention, the tip section 26 carries a plurality of generally equi-sized and equi-angularly spaced, elongated radial electrodes 37$i$. The electrodes 37$i$ are mounted on the tubing 35 of the tip section 26 and in a side-by-side configuration to jointly span about 360 degrees around the tubing 35. A longitudinal gap between each radial electrodes is provided to electrically isolate each radial electrode from its adjacent radial electrodes. The gap may be filled with a non-conducting material 43, for example, polyurethane. As such, the electrodes 37$i$ cover nearly the entire circumference of the tubing. Moreover, the distal ends of the electrodes 37$i$ are immediately proximal the tip electrode such that the tip electrode 28 and at least one radial electrode 37$i$ form a generally continuous elongated contact surface 53 with tissue 54 when the tip section 26 is oriented at a nonperpendicular angle. As shown in FIG. 5, the radial electrode 37$b$ together with the tip electrode 28 enable the creation of a larger lesion 59 by providing a larger, generally continuous contact surface 53 with the tissue 54. Depending on the tissue surface contour, the size of the generally continuous contact surface 53 is typically at a minimum where the tip section 26 is generally perpendicular or about 90 degrees to the tissue surface 55 and increases with decreasing angle of the tip section 28 to the tissue surface 55, with a maximum contact surface area where tip section 26 is generally parallel with the tissue surface 55, lying on it, at or about 0 degrees.

As discussed further below, the present invention provides for selective energization of the radial electrode (e.g., electrode 37$b$ in FIG. 5) that has the most tissue contact for improved energy efficiency during ablation. That is, by withholding the ablation energy from those radial electrodes with less or no tissue contact (e.g., electrodes 37$a$, 37$c$ and 37$d$ in FIG. 5), the energy is applied with discretion to minimize energy loss to the surrounding blood. In accordance with a feature of the invention, by providing n number of radial electrodes 37$a$-37$n$, each radial electrode possesses a (1/n) fraction of the circumferential tissue contact surface of the catheter tip section. And, by supplying the ablation energy through only one radial electrode (namely, the one having the greatest tissue contact), the 1/n surface area of that radial electrode, by definition, increases the current density, whereupon a higher current density permits lower power usage and greater efficiency by the catheter 10.

Because of the location of the tip electrode, it generally makes good tissue contact, particularly, when it is depressed into the tissue as shown in FIG. 5. Accordingly, in the disclosed embodiment, the tip electrode 28 consistently receives the ablation energy whenever the ablation energy is applied by the operator and is not subject to this discretionary process.

Moreover, by selectively energizing the radial electrodes, the tip section 26 is rendered less prone to overheating and therefore the tissue is less susceptible to the risks associated with overheating, such as char and thrombus.

It is understood by one of ordinary skill in the art that the number of radial electrodes may be varied and can range between at least two to about eight, provided the electrodes jointly span about 360 degrees around the tubing 35 to cover its circumference. In the illustrated embodiment, there are four "quadrant" electrode 37a-37d, each generally rectangular and spanning about 90 degrees around the tubing 35. The length of each radial electrode may range between about 4.0 mm and 10 mm, and preferably is about 8.0 mm. It is understood by one of ordinary skill in the art that the width of each radial electrode depends on the size of the catheter tip section and the number of radial electrodes.

There may also be ring electrodes 56 carried on the distal section of the tubing 19 of the intermediate section 14. In the illustrated embodiment, there are three ring electrodes proximal of the radial electrodes 37. The ring electrodes 56 allow an operator to collect electrophysiological data from the tip section 36 of the catheter 10. Accordingly, the presence and number of ring electrodes 56 can vary as desired.

The tip electrode 28, the radial electrodes 37 and the ring electrodes 56 can be made of any suitable material, for example, from machined platinum-iridium bar (90% platinum/10% iridium).

Each of the tip electrode 28, the radial electrodes 37, and the ring electrodes 56 is connected to a separate lead wire. The lead wires 40, 42 and 44 extend through the first lumen 30 of intermediate section 14, the central lumen 18 of the catheter body 12, and the control handle 16, and terminate at their proximal end in an input jack (not shown) that may be plugged into an appropriate monitor (not shown). The portion of the lead wires 40, 42, 44 extending through the central lumen 18 of the catheter body 12, control handle 16 and the intermediate section 14 are enclosed within a protective, non-conducting sheath 39, which can be made of any suitable material, preferably polyimide. The sheath 39 is anchored at its distal end to the distal end of the intermediate section 14 by gluing it in the first lumen 30 with polyurethane glue or the like. In the illustrated embodiment, there are two sheaths 39A and 39B. The sheath 39A is dedicated to the lead wire 40 for the tip electrode 28 and the lead wires 44 for the ring electrodes 56. The sheath 49B is dedicated to the lead wires 42 for the radial electrodes 37. The distal end of sheath 39B is proximal of the most proximal ring electrode 56. The distal end of the sheath 39A is proximal of the radial electrodes 37.

The lead wires 44 and 42 are attached to the radial and ring electrodes 37 and 56 by any conventional technique. Connection of a lead wire to one of these electrodes is preferably accomplished by first making a small hole through the tubing 19 or 35. Such a hole can be created, for example, by inserting a needle through the tubing and heating the needle sufficiently to form a permanent hole. A lead wire is then drawn through the hole by using a microhook or the like. The ends of the lead wire are then stripped of any coating and soldered or welded to the underside of the electrode. The electrodes may then be positioned over the hole (or slid into position over the hole in the case of the ring electrodes) and are fixed in place with polyurethane glue or the like.

The tip section 26 carries the electromagnetic location sensor 72 which is bonded in the lumen of the tubing 35. The electromagnetic sensor cable 74 extend from the proximal end of the location sensor and through the third lumen 34 of the tip section 14, through the central lumen 18 of the catheter body 12, and into the control handle 16. As shown in FIG. 1, the electromagnetic sensor cable 74 then extends out the proximal end of the control handle 16 within an umbilical cord 98 to a sensor control module 75 that houses a circuit board (not shown). Alternatively, the circuit board can be housed within the control handle 16, for example, as described in U.S. Pat. No. 5,964,757, the entire disclosure of which is incorporated herein by reference. The electromagnetic sensor cable 74 comprises multiple wires encased within a plastic covered sheath. In the sensor control module 75, the wires of the electromagnetic sensor cable 74 are connected to the circuit board. The circuit board amplifies the signal received from the electromagnetic sensor 72 and transmits it to a computer in a form understandable by the computer by means of the sensor connector 77 at the proximal end of the sensor control module 75, as shown in FIG. 1. Also, because the catheter is designed for single use only, the circuit board may contain an EPROM chip which shuts down the circuit board approximately 24 hours after the catheter has been used. This prevents the catheter, or at least the electromagnetic sensor, from being used twice. Suitable electromagnetic sensors for use with the present invention are described, for example, in U.S. Pat. Nos. 5,558,091, 5,443,489, 5,480, 422, 5,546,951, 5,568,809, and 5,391,199 and International Publication No. WO 95/02995, the disclosures of which are incorporated herein by reference. A preferred electromagnetic mapping sensor 72 has a length of from about 6 mm to about 7 mm and a diameter of about 1.3 mm.

Referring back to FIG. 2, the puller wire 50 extends through the catheter body 12, is anchored at its proximal end to the control handle 16 (FIG. 6), and is anchored at its distal end to the tip electrode 28 (FIG. 4A). The puller wire is made of any suitable metal, such as stainless steel or Nitinol, and preferably has a coating of Teflon® or the like. The coating imparts lubricity to the puller wire. The puller wire preferably has a diameter ranging from about 0.006 to about 0.010 inches.

A compression coil 52 is situated within the catheter body 12 in surrounding relation to the puller wire 50. The compression coil 52 extends from the proximal end of the catheter body 12 to the proximal end of the intermediate section 14. The compression coil 52 is made of any suitable metal, preferably stainless steel. The compression coil 52 is tightly wound on itself to provide flexibility, i.e., bending, but to resist compression. The inner diameter of the compression coil is preferably slightly larger than the diameter of the puller wire 50. The Teflon® coating on the puller wire 50 allows it to slide freely within the compression coil 52. If desired, particularly if the lead wires 40, 42, 44 are not enclosed by a protective sheaths 39, the outer surface of the compression coil can be covered by a flexible, non-conductive sheath, e.g., made of polyimide tubing, to prevent contact between the compression coil 52 and any other wires within the catheter body 12.

The compression coil 52 is anchored at its proximal end to the proximal end of the stiffening tube 22 in the catheter body 12 by glue joint 51 and at its distal end to the intermediate section 14 by glue joint 57. Both glue joints 51 and 57 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 and the stiffening tube 22 which is heated sufficiently to form a permanent hole. The glue is then introduced through the hole to the outer surface of the compression coil 52 and wicks around the outer circumference to form a glue joint about the entire circumference of the compression coil 52.

As shown in FIG. 4A, the puller wire 50 is anchored at its distal end to the tip electrode 28 within the blind hole 31. A preferred method for anchoring the puller wire 50 within the tip electrode 28 is by crimping metal tubing 46 to the distal end of the puller wire 50 and soldering the metal tubing 46 inside the blind hole 31. Anchoring the puller wire 50 within the tip electrode 28 provides additional support, reducing the likelihood that the tip electrode 28 will fall off the tip section 26. Alternatively, the puller wire 50 can be attached to the tubing 35 of the tip section 26, or the distal section of the tubing 19 of the intermediate section 14. Within the second lumen 32 of the intermediate section 14, the puller wire 50 extends through a plastic, preferably Teflon®, sheath 58, which prevents the puller wire 50 from cutting into the wall of the tubing 19 when the intermediate section 14 is deflected.

Figure 6:
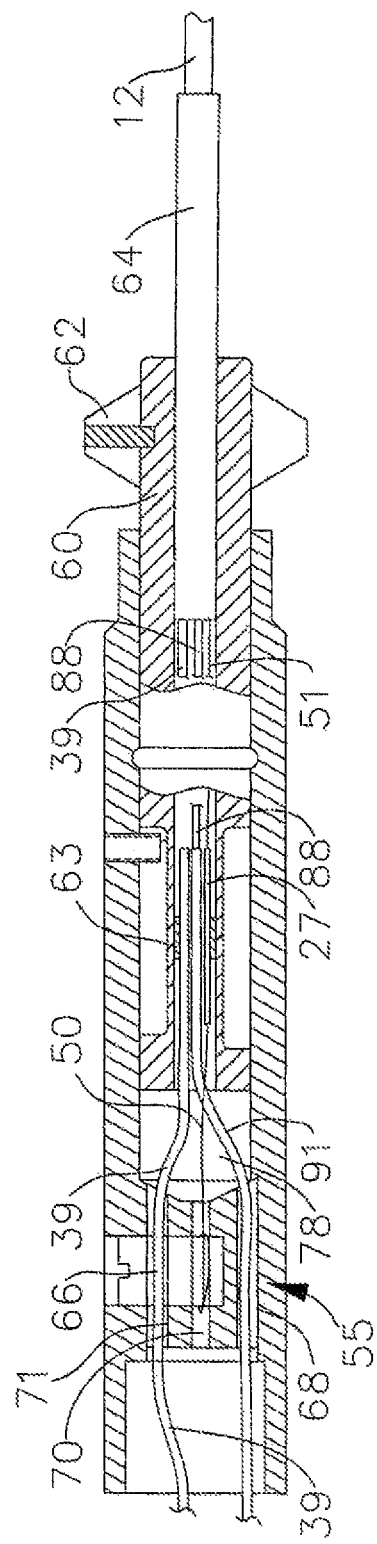
FIG. 6 is a side cross-sectional view of an embodiment of a control handle.

Longitudinal movement of the puller wire 50 relative to the catheter body 12, which results in deflection of the intermediate section 14, is accomplished by suitable manipulation of the control handle 16. As shown in FIG. 6, the distal end of the control handle 16 comprises a piston 60 with a thumb control 62 for manipulating the puller wire 50. The proximal end of the catheter body 12 is connected to the piston 60 by means of a shrink sleeve 64.

The puller wire 50, lead wires 40, 42, 44, the sensor cable 74 extend through the piston 60. The puller wire 50 is anchored to an anchor pin 66, located proximal to the piston 60. Within the piston 60, the sensor cable 74 extends into another protective sheath 91, preferably made of polyurethane. The protective sheathes 39A, 39B and 91 are anchored to the piston 60, preferably by polyurethane glue or the like at a glue joint 63, allowing the lead wires 40, 42, 44 and the sensor cable 74 longitudinal movement within the control handle 16 so that they do not break when the piston 60 is adjusted to manipulate the puller wire 50. Within the piston 60, the puller wire 50 extends through a transfer tube 27, preferably a polyimide tube, to allow longitudinal movement of the puller wire near the glue joint 63.

The mechanics and operation of the control handle are described in U.S. Pat. No. 6,602,242, the entire disclosure of which is incorporated herein by reference. It is understood by one of ordinary skill in the art that other control handles for manipulating the puller wire or puller wires (for bi-directional deflection) may be used with the present catheters.

Figure 7:
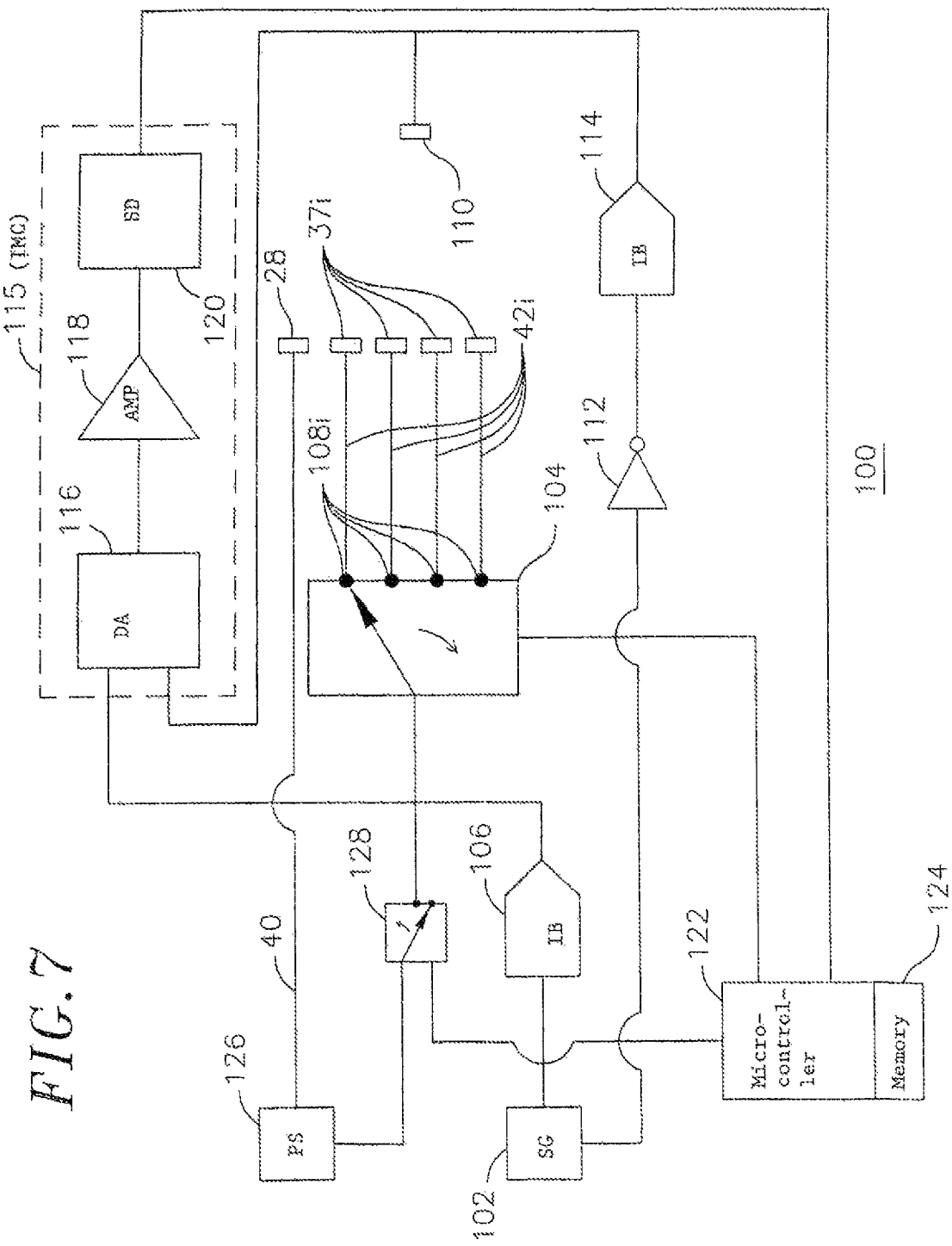
FIG. 7 is a schematic diagram of an embodiment of a system for selectively energizing catheter electrodes in accordance with the present invention.

FIG. 7 illustrates a system 100 for performing ablation using the catheter 10 in selectively energizing the radial electrode having the greatest tissue contact as identified by the system on the basis of impedance measurements. Each of the radial electrodes 37$i$ is connected by a separate lead wire 42$i$ to the catheter handle 16 from which electrical connections are made to the system 100. A signal generator (SG) 102 sends a high frequency test signal, e.g., an alternating current (AC) signal at about 2 μamps, in the frequency range of about 10 kHz to about 100 kHz, preferably about 50 kHz, to a multiplexer 104 via a high output impedance buffer (IB) 106. The multiplexer 104 has multiple channels 108$i$, each of which is in communication with a specific radial electrode 37$i$ to receive the same current.

A return electrode 110 is also driven by the signal generator 102. The signal to the return electrode 110 is first inverted in phase by inverter 112 and conditioned by high output impedance buffer (IB) 114.

In accordance with a feature of the invention, the system 100 provides an impedance measurement circuitry (IMC) 115 to measure the impedance of each radial electrode as an indicator of the extent of tissue contact of each radial electrode. By energizing only the radial electrode with the greatest impedance measurement, that selected radial electrode and the tip electrode form a greater tissue contact surface than the tip electrode would by itself and the ablation energy is not wasted on other radial electrodes that have no or lesser tissue contact. The impedance measurement circuitry 115 includes a differential amplifier (DA) 116, an amplifier (AMP) 118 and a synchronous detector (SD) 120. The differential amplifier 116 measures a difference signal, specifically the voltage across a selected radial electrode 37$i$ and the return electrode 110. The difference signal is further amplified by the amplifier 118 whose output is send to the synchronous detector 120 which transforms the AC signal into a direct current (DC) signal and also decreases the sensitivity of the system 100 to external noise. The signal from the synchronous detector 120 is then used by a microcontroller 122 to control the multiplexer 104. To that end, the microcontroller continuously stores in a memory 124 a plurality of different impedance signals from the synchronous detector 120 that equals the plurality of channels 108$i$ in the multiplexer 104 (which is at least the plurality of radial electrodes 37$i$ on the catheter 10), along with identification information on the channels 108$i$ associated with each impedance value stored. As such, the microcontroller 122 is at any time capable of identifying the channel 108$i$ (and hence the radial electrode 37$i$) exhibiting the highest impedance value, which should be the radial electrode 37$i$ with the greatest tissue contact.

Figure 8:
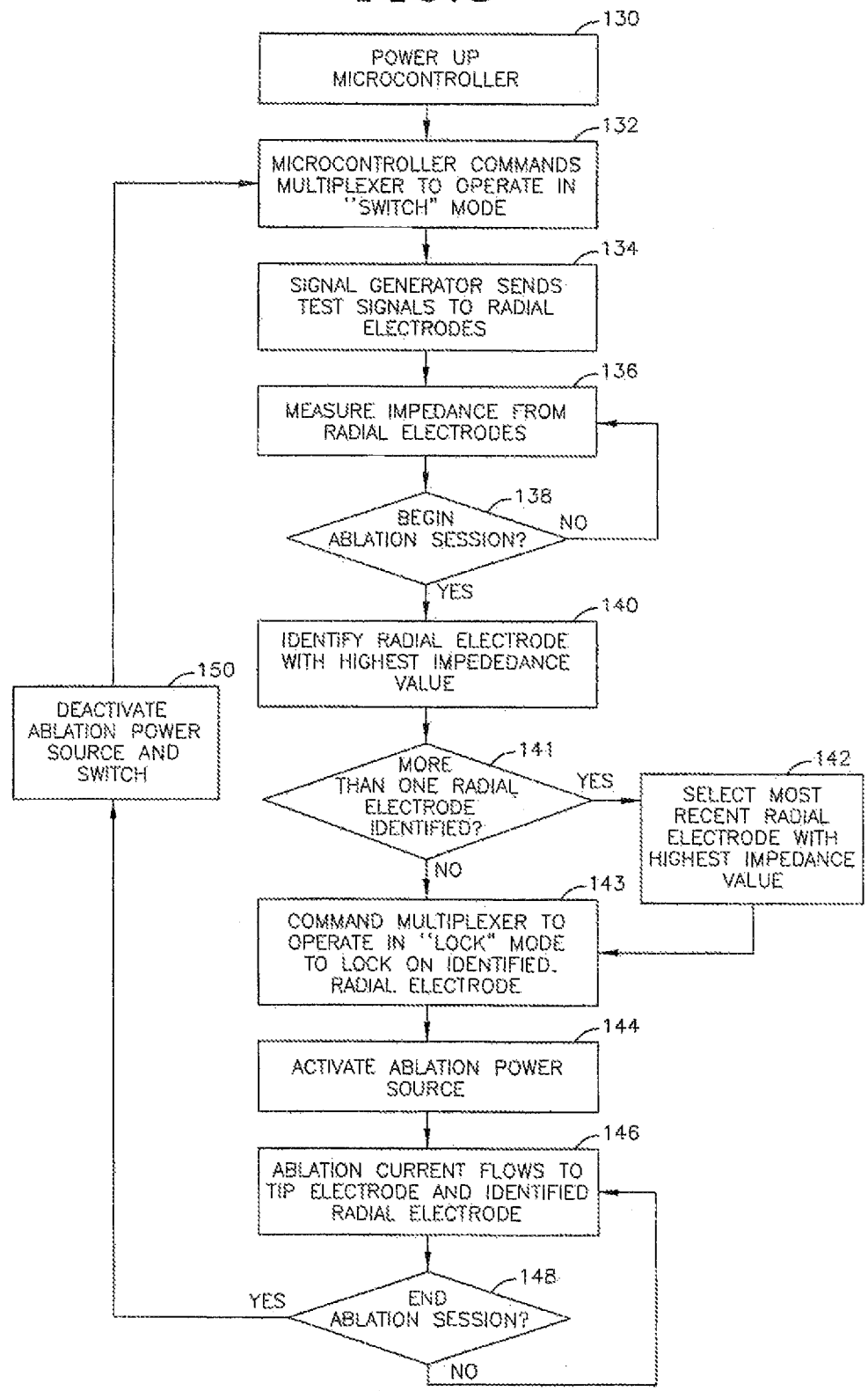
FIG. 8 is a flow chart illustrating schematically a method of selectively energizing catheter electrodes in accordance with the present invention.

With reference to the flow chart of FIG. 8, the system 100 in operation as implemented by the microcontroller 122 is described as follows. Under fluoroscopic guidance, or other suitable guidance means, the catheter is introduced into the patient's body. The catheter is advanced into the patient's heart through appropriate vascular access and positioned inside the heart chamber. The system 100 and microcontroller 122 are powered up (Block 130). The microcontroller 122 is activates the signal generator and commands the multiplexer to operate in the "switch" mode (Block 132), whereby the multiplexer constantly switches between the channels 108$i$ and allows passage of the impedance test signal from the signal generator 102 to only one radial electrode 37$i$ at any given time (Block 134). The impedance measurement circuitry 115 measures the impedance of each radial electrode 37$i$ as the multiplexer 108 switches between the different channels 108$i$ (Block 136) and the impedance measurements are stored in the memory which is constantly being updated with new impedance measurements of each radial electrode.

When the operator of the catheter is ready to ablate, he triggers an input, e.g., a push-to-activate contact 129 (FIG. 7) or the like (Query 138), which signals the microcontroller 122 to access the memory 124 and identify the channel 108 with the greatest impedance value (Block 140). If there are more than one radial electrode with the same greatest impedance measurement (Block 141), the microcontroller 122 selects the most recent radial electrode with the greatest impedance measurement (Block 142). In any event, the microcontroller 122 then commands the multiplexer 104 to switch to a "lock" (or "stationary") mode and the connection of the multiplexer remains on the identified channel (Block 143) for the duration of the ablation session.

The microcontroller 122 then enables the ablation power source (PS) 126 and the switch 128 (Block 144) which energizes the tip electrode 28 and allows the ablation current to pass to the selected radial electrode whose lead is receiving the current from the multiplexer 104 (Block 146). The combined contact surface of the tip electrode 28 and the selected radial electrode 37$i$ creates a larger lesion with improved energy efficiency because the ablation current is directed to the tip electrode 28 and only the radial electrode 37$i$ with the most tissue contact.

When the operator completes the ablation session, he releases the button or switch and the microcontroller 122 deactivates the ablation power source 126 and the switch 128 (Block 150) and returns the multiplexer 104 to operation in the "switch" mode (Block 132). Thus, the multiplexer 104 returns to constantly switching between its channel 108$i$ to allow the test signal from the signal generator 102 to pass through the different channels onto each radial electrode 37*i*. The microcontroller 122 returns to receiving impedance signals of each radial electrode 37*i* from the impedance measurement circuitry 115 and constantly storing and refreshing the impedance values in the memory 124, along with the identification information of the channel associated with each stored impedance values.

The preceding description has been presented with reference to presently preferred embodiments of the invention. Workers skilled in the art and technology to which this invention pertains will appreciate that alterations and changes to the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support for the following claims which are to have their fullest and fairest scope.

What is claimed is:

1. A catheter comprising:
   an elongated catheter body;
   a tip section having a tip electrode and a plurality of radial electrodes proximal of and immediately adjacent to the tip electrode such that each of the radial electrodes forms a different continuous elongated electrode surface with the tip electrode.

2. The catheter of claim 1, wherein the radial electrodes span side-by-side radially around the tip section, each separated from adjacent radial electrodes by a gap.

3. The catheter of claim 2, wherein the gap includes a non-conducting material.

4. The catheter of claim 1, wherein the plurality of radial electrodes is about four.

5. The catheter of claim 1, wherein the radial electrodes are generally equi-sized.

6. The catheter of claim 1, wherein the radial electrodes are generally equi-angular about the tip section.

7. The catheter of claim 1, further comprising: a different lead wire for each radial electrode.

8. The catheter of claim 1, wherein each radial electrode is separated from adjacent radial electrodes by a nonconducting material.

9. The catheter of claim 1, wherein the radial electrodes have an elongated form extending longitudinally along the tip section.

10. The catheter of claim 1, further comprising at least one ring electrode.

11. The catheter of claim 1, further comprising a first lead wire connected to the tip electrode and a plurality of second lead wires, each second lead wire connected to a different radial electrode.

12. The catheter of claim 1, wherein the radial electrodes are configured such that a specific radial electrode has more surface in contact with the tissue than each of all remaining radial electrodes when the tip electrode is in tissue contact and tilted off-axis against the tissue.

* * * * *